(12) United States Patent
Ichikawa

(10) Patent No.: US 7,219,996 B2
(45) Date of Patent: May 22, 2007

(54) FUNDUS CAMERA

(75) Inventor: Naoki Ichikawa, Gamagori (JP)

(73) Assignee: Nidek Co., Ltd., Gamagori-shi (JP)

( * ) Notice: Subject to any disclaimer, the term of this patent is extended or adjusted under 35 U.S.C. 154(b) by 440 days.

(21) Appl. No.: 10/946,076

(22) Filed: Sep. 22, 2004

(65) Prior Publication Data

US 2005/0068496 A1    Mar. 31, 2005

(30) Foreign Application Priority Data

Sep. 25, 2003    (JP)    ............................ 2003-334439

(51) Int. Cl.
    *A61B 3/14*    (2006.01)
(52) U.S. Cl. ...................................... 351/206; 351/208
(58) Field of Classification Search ........ 351/203–213; 396/14, 18, 106, 323
    See application file for complete search history.

(56) References Cited

U.S. PATENT DOCUMENTS

| 5,463,430 | A | 10/1995 | Isogai et al. ................. 351/211 |
| 6,574,432 | B2 * | 6/2003 | Nanjyo .......................... 396/18 |
| 6,669,339 | B2 * | 12/2003 | Nanjyo ....................... 351/206 |
| 7,052,134 | B2 * | 5/2006 | Nanjo et al. ................. 351/206 |
| 2002/0025145 | A1 | 2/2002 | Nanjyo ........................ 351/206 |

FOREIGN PATENT DOCUMENTS

| JP | A 07-088082 | 4/1995 |
| JP | A 2000-5131 | 1/2000 |

* cited by examiner

*Primary Examiner*—Hung Xuan Dang
*Assistant Examiner*—M. Hasan
(74) *Attorney, Agent, or Firm*—Oliff & Berridge, PLC

(57) ABSTRACT

A fundus camera capable of performing accurate and easy focusing in photographing a peripheral portion of a fundus has a photographing optical system including a photographing optical axis, a focusing lens movable in a direction of the photographing optical axis and an image-pickup element, a lens moving unit, a focus target projection optical system, a focus target detection optical system, a fixation target presenting unit, in which a presenting position of the fixation target is changeable between a reference position for photographing a central portion of the fundus and a position for photographing a peripheral portion, a device which controls the lens moving unit to perform automatic focusing, and a device which controls the fixation target presenting unit to bring the presenting position of the fixation target to the reference position when the automatic focusing is actuated, even though the presenting position is set to the peripheral position.

5 Claims, 8 Drawing Sheets

FUNDUS CAMERA

BACKGROUND OF THE INVENTION

1. Field of the Invention

The present invention relates to a fundus camera for photographing a fundus of an eye to be examined.

2. Description of Related Art

For a fundus camera, accurate alignment with an eye to be examined (a patient's eye) and accurate focusing on a fundus are important to photograph the fundus favorably. As for focusing, a method for projecting a split target or the like onto the fundus to move a focusing lens based on the target is suggested, for example, in Japanese Patent Application Unexamined Publication No. 2000-5131. Also, to photograph the fundus extensively, a presenting position of a fixation target (a fixation light source) for guiding a line of sight of the eye is moved so that a central portion and a peripheral portion of the fundus are photographed.

However, when the presenting position of the fixation target is set in a position for photographing the peripheral portion of the fundus, a visual axis of the eye deviates widely from a photographing optical axis, and the target for focusing may chip or blur, so that there is a case where accurate focusing cannot be performed.

SUMMARY OF THE INVENTION

An object of the invention is to overcome the problems described above and to provide a fundus camera capable of performing accurate and easy focusing also in photographing a peripheral portion of a fundus.

To achieve the objects and in accordance with the purpose of the present invention, a fundus camera for photographing a fundus of an eye to be examined is provided with a photographing optical system having a photographing optical axis, a focusing lens movable in a direction of the photographing optical axis and an image-pickup element, a lens moving unit which moves the focusing lens in the photographing optical axis direction, a focus target projection optical system for projecting a focus target onto the fundus, a focus target detection optical system for detecting the projected focus target, a fixation target presenting unit which presents a fixation target for guiding a line of sight to the eye, in which a presenting position of the fixation target is changeable between a reference position which is a position for photographing a central portion of the fundus and a peripheral position which is a position for photographing a peripheral portion of the fundus, focusing control means for controlling the lens moving unit based; on a detection result of the focus target to perform automatic focusing of the photographing optical system with respect to the fundus, and fixation target presentation control means for controlling the fixation target presenting unit so that the presenting position of the fixation, target is brought to the reference position when the automatic focusing is actuated, even though the presenting position of the fixation target is set in the peripheral position.

Additional objects and advantages of the invention areset forth in the description which follows, are obvious from the description, or may be learned by practicing the invention. The objects and advantages of the invention may be realized and attained by the fundus camera in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
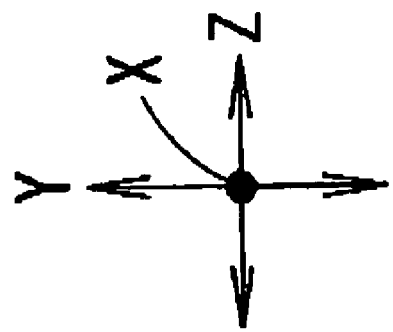
FIG. 1 is a view showing a schematic configuration of a fundus camera.
Figure 1:
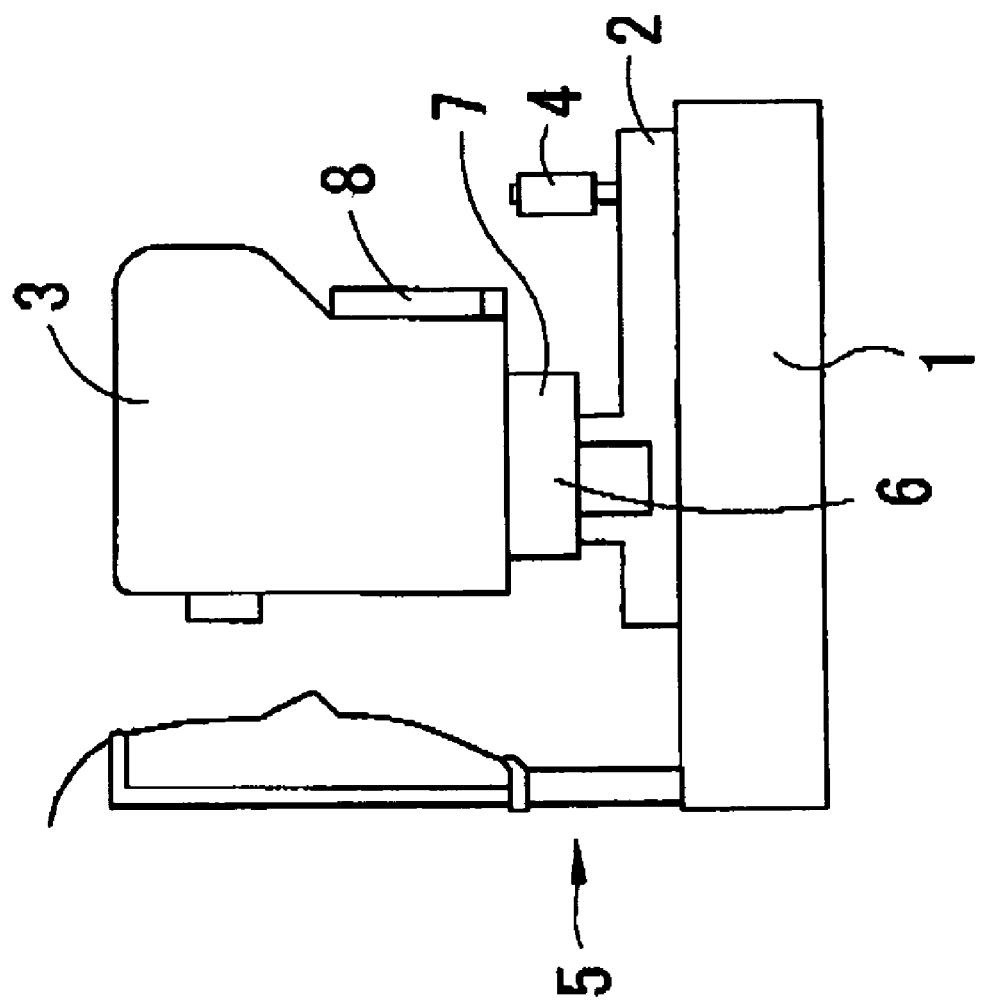

A detailed description of one preferred embodiment of a fundus camera embodied by the present invention is provided below with reference to the accompanying drawings. FIG. 1 is a view showing a schematic configuration of a fundus camera consistent with the preferred embodiment of the present invention.

The fundus camera is provided with a base 1, a moving base 2 being movable in a right-and-left direction (hereinafter referred to as an "X-direction") and a back-and-forth direction (hereinafter referred to as a "Z-direction") with reference to the base 1 by operation of a joystick 4, a photographing unit 3 being movable in the right-and-left direction, an up-and-down direction (hereinafter referred to as a "Y-direction"), and the back-and-forth direction with reference to the moving base 2 under control of a control unit 90, and a face supporting unit 5 fixedly arranged on the base 1 for supporting a face of an examinee. In an X-and Z-moving unit 7, a Z table movable in the Z-direction is arranged on a Y table, an X table movable in the X-direction is arranged on the Z tables and the photographing unit 3 is arranged on the X table. The X-and Z-moving unit 7 moves the X and Z tables by their respective moving mechanisms consisting of a motor and the like to move the photographing unit 3 in the X-and Z-directions. A Y-moving unit 6 moves the Y table by its moving mechanism consisting of a motor and the like to move the photographing unit 3 in the Y-direction. Besides, for this kind of three-dimensional moving mechanism, a known mechanism may be employed. Further, the photographing unit 3 is moved in the Y-direction also by actuating the Y-moving unit 6 through operation of a rotary knob of the joystick 4. A monitor 8 for displaying an observation image and a photographed image is provided on an examiner's side of the photographing unit 3.

Figure 2:
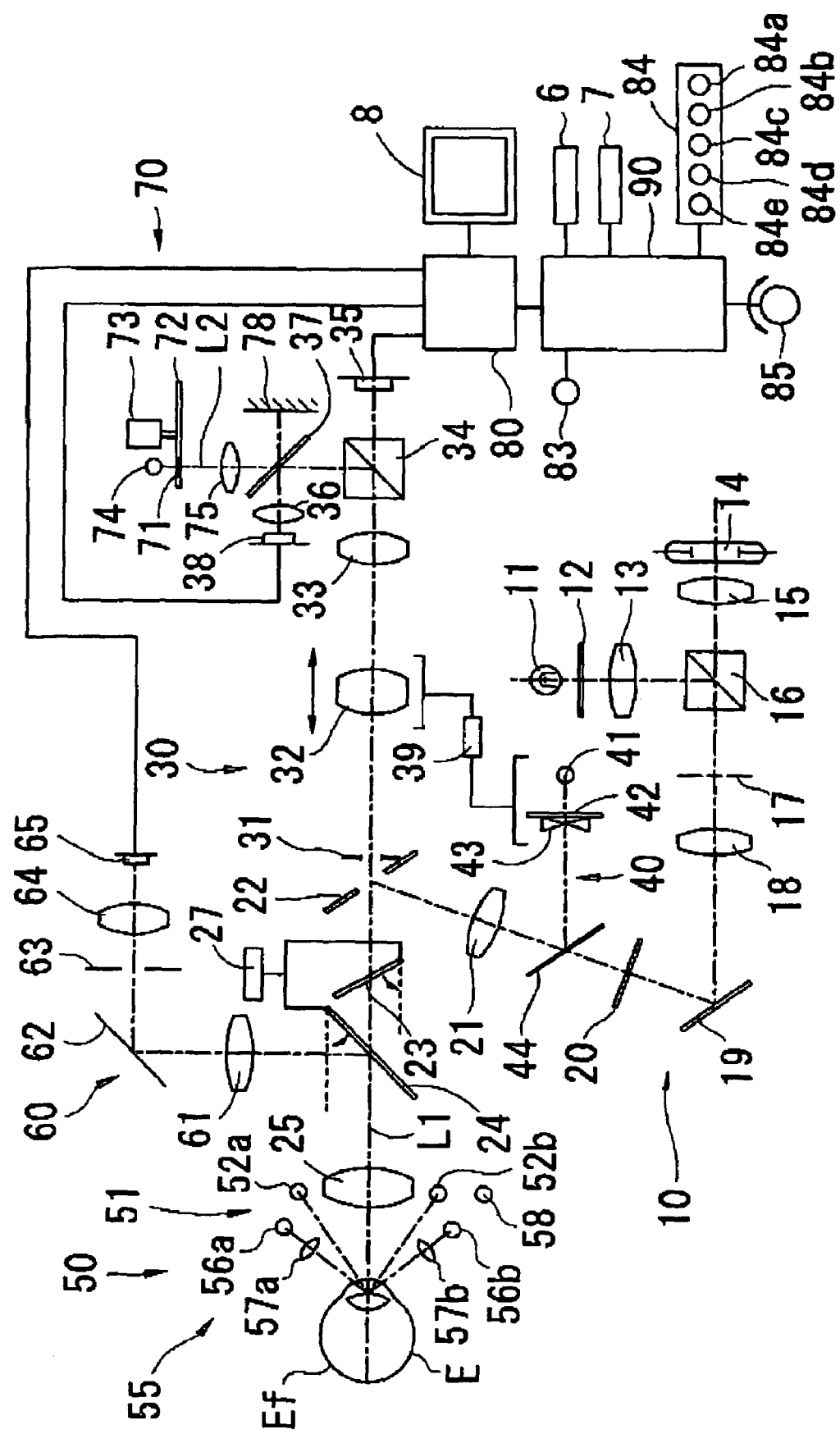
FIG. 2 is a view showing a schematic configuration of an optical system and a control system of the fundus camera.

FIG. 2 is a view showing a schematic configuration of an optical system and a control system housed in the photographing unit 3. The optical system roughly consists of an illumination optical system 10, a fundus observation/photographing optical system 30, a focus target projection optical system 40, an alignment target projection optical system 50, an anterior-segment observation optical system 60 and a fixation target presenting optical system 70.

<Illumination Optical System 10>

The illumination optical system 10 includes an illumination optical system for fundus observation and an illumination optical system for photographing. Illumination light emitted from an illumination light source 11 for fundus observation such as a halogen light is made infrared illumination light by an infrared transmission filter 12 which transmits light within an infrared wavelength range of approximately 750 nm to approximately 880 nm, and reflected by a dichroic mirror 16 via a condenser lens 13. The dichroic mirror 16 has a wavelength-selecting property of reflecting approximately all light within an infrared wavelength range and transmitting approximately all light within a visible wavelength range. The infrared illumination light reflected by the dichroic mirror 16 passes though a slit plate 17, a relay lens 18, a reflection mirror 19, a black dot plate 20 having a black dot at its center, a half mirror 44 and a relay lens 21, and is reflected by an apertured mirror 22 to be projected onto a fundus Ef of an eye E of the examinee via an objective lens 25. The slit plate 17 has a pinhole opening (aperture) at its center part (on an optical axis) with a ring-slit opening (aperture) therearound. Besides, an infrared light source such as an infrared light-emitting diode may be used instead of the light source 11 such as a halogen light and the infrared transmission filter 12.

Visible illumination light emitted from a visible illumination light source 14 for photographing such as a flash light passes through a condenser lens 15 and is transmitted through the dichroic mirror 16 to be projected onto the fundus Ef of the eye E via the slit plate 17 to the objective lens 25.

<Fundus Observation/Photographing Optical System 30>

The fundus observation/photographing optical system 30 includes a fundus observation optical system and a photographing optical system. Infrared reflection light and visible reflection light from the fundus Ef of the eye E pass through the objective lens 25, an opening (aperture) of the apertured mirror 22, a photographing diaphragm 31 arranged in the vicinity of the opening of the mirror 22, a focusing lens 32 and an image forming lens 33 to enter a dichroic mirror 34. The photographing diaphragm 31 is arranged in a position approximately conjugate with a pupil of the eye E with reference to the objective lens 25. The focusing lens 32 is arranged movable by a moving mechanism 39 consisting of a motor and the like in a direction of an optical axis L1 of the fundus observation/photographing optical system 30 (i.e., an optical axis of the objective lens 25). The dichroic mirror 34 has a wavelength-selecting property of reflecting approximately all light within the infrared wavelength range, and reflecting a part (a small proportion) of light within the visible wavelength range and transmits the other part (a large proportion). The visible reflection light transmitted through the dichroic mirror 34 is photo-received on a CCD camera 35 for photographing having sensitivity to the visible wavelength range to form an image of the fundus Ef of the eye E. Also, the infrared reflection light reflected by the dichroic mirror 34 is reflected by a dichroic-mirror 37, and photo-received on a CCD camera 38 for fundus observation having sensitivity to the infrared wavelength range via a relay lens 36 to form an image of the fundus Ef of the eye E. The dichroic mirror 37 has a wavelength-selecting property of reflecting approximately all light within the infrared wavelength range, and reflecting apart (a small proportion) of light within the visible wavelength range and transmits the other part (a large proportion). Besides, the CCD-camera 38, which doubles as image-pickup means for focus target detection to be described later (i.e., the fundus observation optical system doubles as a focus target detection optical system), picks up the image of the fundus Ef formed by the light source 11 and an image of the focus target formed by the focus target projection optical system 40 to be described later.

On an optical path between the objective lens 25 and the apertured mirror 22 (the diaphragm 31), a movable dichroic mirror 24 is arranged as an optical path dividing member. Further, on an optical path between the dichroic mirror 24 and the apertured mirror 22 (the diaphragm 31), a movable parallel glass plate 23 is arranged as a member for correcting a deviation of an optical axis caused by the dichroic mirror 24. The dichroic mirror 24 has a wavelength-selecting property of reflecting approximately all light within an infrared wavelength range of approximately 900 nm or more including light from an illumination light source 58 for anterior-segment observation and that from the alignment target projection optical system 50, to be described later, and transmitting approximately all light within an infrared wavelength range of approximately 900 nm or less including light from the illumination optical system for fundus observation and that from the focus target projection optical system 40 to be described later. The glass plate 23 has approximately the same thickness and refractive index as the dichroic mirror 24. At the time of photographing, the dichroic mirror 24 and the glass plate 23 are flipped up synchronously by an inserting and removing mechanism 27 to be removed from the optical path. Besides, a known mechanism such as a solenoid and cam (or motor and the like) may be used for the inserting and removing mechanism 27.

<Focus Target Projection Optical System 40>

Infrared target light emitted from an infrared light source 41 for focus target projection such as an infrared light-emitting diode passes through a slit target plate 42 and two deflection-angle prisms 43 attached to the target plate 42, and is reflected by the half mirror 44, and further passes through the relay lens 21 to the objective lens 25 to be projected onto the fundus Ef of the eye E. The light source 41 and the target plate 42 are moved in synchronization with the focusing lens 32 in the optical axis direction by the moving mechanism 39. Incidentally, the light source 41 emits infrared light having a center wavelength of approximately 880 nm.

<Alignment Target Projection Optical System 50>

The alignment target projection optical system 50 includes a first projection optical system 51 and a second projection optical system 55. The first projection optical system 51 includes infrared light sources 52a and 52b such as infrared light-emitting diodes arranged vertically symmetrical with respect to the optical axis L1, and projects infrared target light at a finite distance onto a cornea of the eye E. The second projection optical system 55 includes infrared light sources 56a and 56b such as infrared light-emitting diodes and collimating lenses 57a and 57b arranged laterally symmetrical with respect to the optical axis L1, and projects infrared target light at an infinite distance onto the cornea of the eye E. Incidentally, the light sources 52a, 52b, and 56a, 56b emit infrared light having a center wavelength of approximately 940 nm.

<Anterior-Segment Observation Optical System 60>

Infrared illumination light emitted from the illumination light source 58 for anterior-segment observation such as an infrared light-emitting diode is reflected by an anterior-segment of the eye E and the dichroic mirror 24, and passes through a field lens 61, a reflection mirror 62, a diaphragm 63 and a relay lens 64, and is photo-received on a CCD camera 65 having sensitivity to the infrared wavelength range to form an image of the anterior-segment of the eye E. Besides, the light source 58 emits infrared light having a center wavelength of approximately 940 nm. Further, the CCD camera 65, which doubles as image-pickup means for alignment target detection (i.e., the anterior-segment observation optical system 60 doubles as an alignment target detection optical system), picks up the image of the anterior-segment of the eye E-formed by the light source 58 and an image of an alignment target formed by the alignment target projection optical system 50.

<Fixation Target Presenting Optical System 70>

Figure 3:
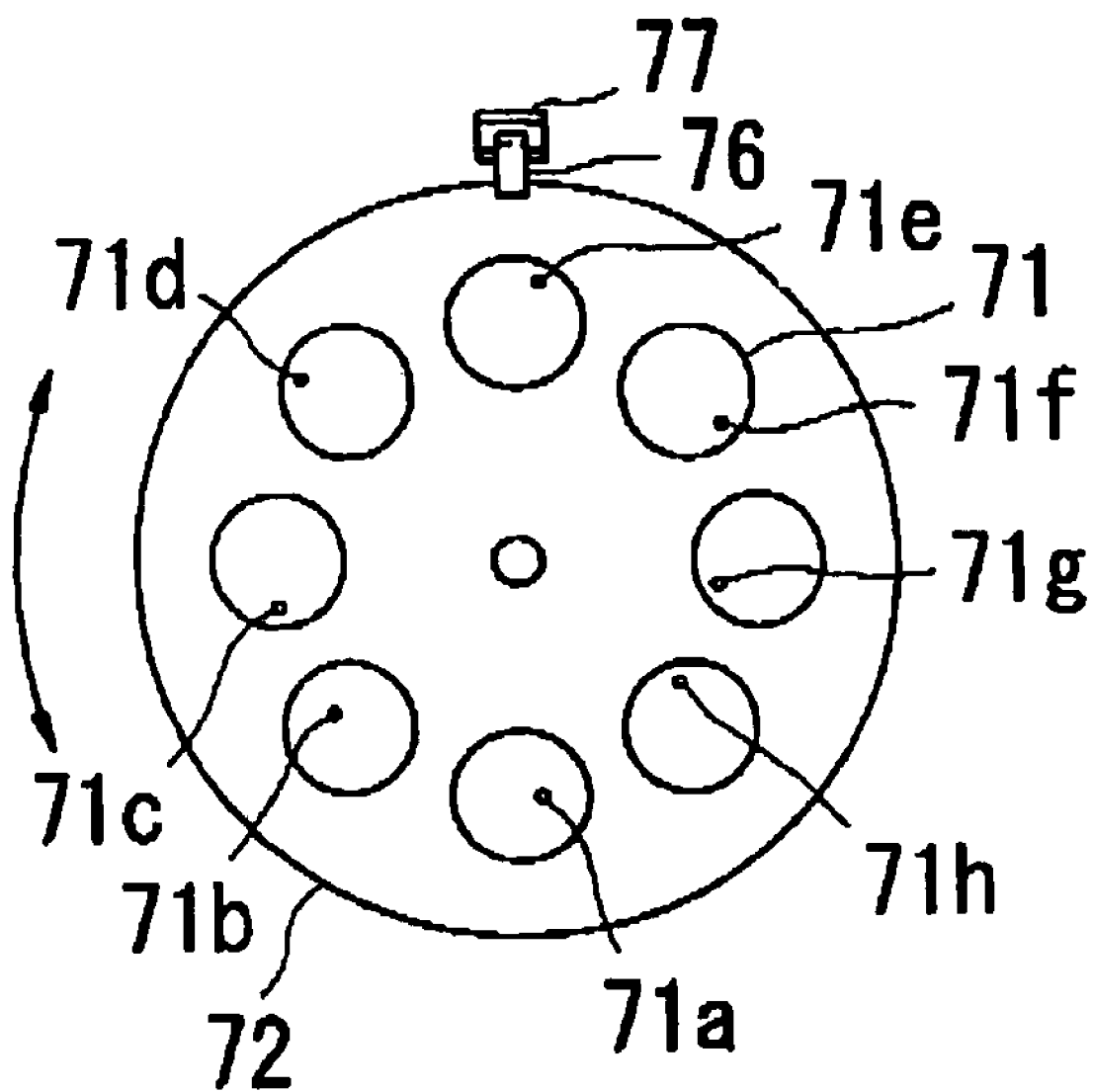
FIG. 3 is a view showing a schematic configuration of a rotary disk in a fixation target presenting optical system.
Figure 4A:
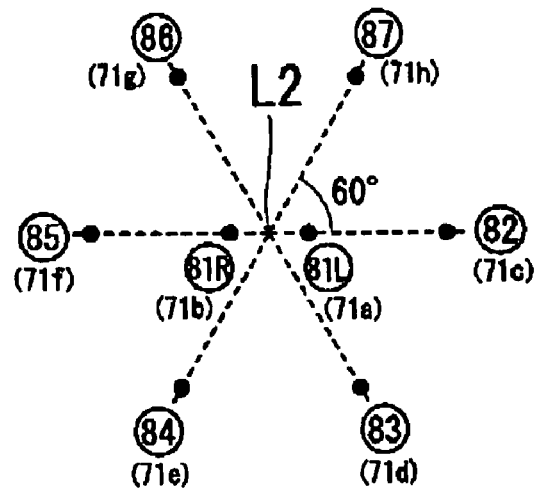
FIGS. 4A and 4B are views showing presenting positions of a fixation target and their corresponding regions on a fundus to be photographed.

Red fixation target light emitted from a fixation target light source (a fixation lamp) 74 such as a red light-emitting diode passes through an opening (aperture) in a shielding plate 71 of a rotary disk 72 and a relay lens 75 to be transmitted through the dichroic mirror 37. A part of the red fixation target light transmitted through the dichroic mirror 37 is reflected by the dichroic mirror 34 to be projected onto the fundus Ef of the eye E via the image forming lens 33 to the objective lens 25. As shown in FIG. 3, the disk 72 includes the eight shielding plates 71, respectively provided with openings (apertures) 71*a*–71*h*. The disk 72 is rotated by a pulse motor 73, and one of the eight shielding plates 71 is selectively arranged in front of the light source 74. As shown in FIG. 4A, such a selective arrangement of the shielding plates 71 allows a fixation target to be presented in eight positions 81L, 81R and 82–87 corresponding to the eight openings 71*a*–71*h* with respect to an optical axis L2 of the fixation target presenting optical system 70 (i.e., an optical axis of the relay lens 75). Besides, the optical axis L2 is made coaxial (or, it has a predetermined positional relationship) with the optical axis L1. An initial position for rotation of the disk 72 is detected through a shielding plate 76 and an optical sensor 77 provided with and a photo-projecting/receiving part. A control unit 90 controls a rotation angle by the pulse motor 73 so that each of the openings 71*a*–71*h* may be arranged in front of the light source 74. The number of pulses for arranging each of the openings 71*a*–71*h* in front of the light source 74 is previously stored in the control unit 90.

Figure 4B:
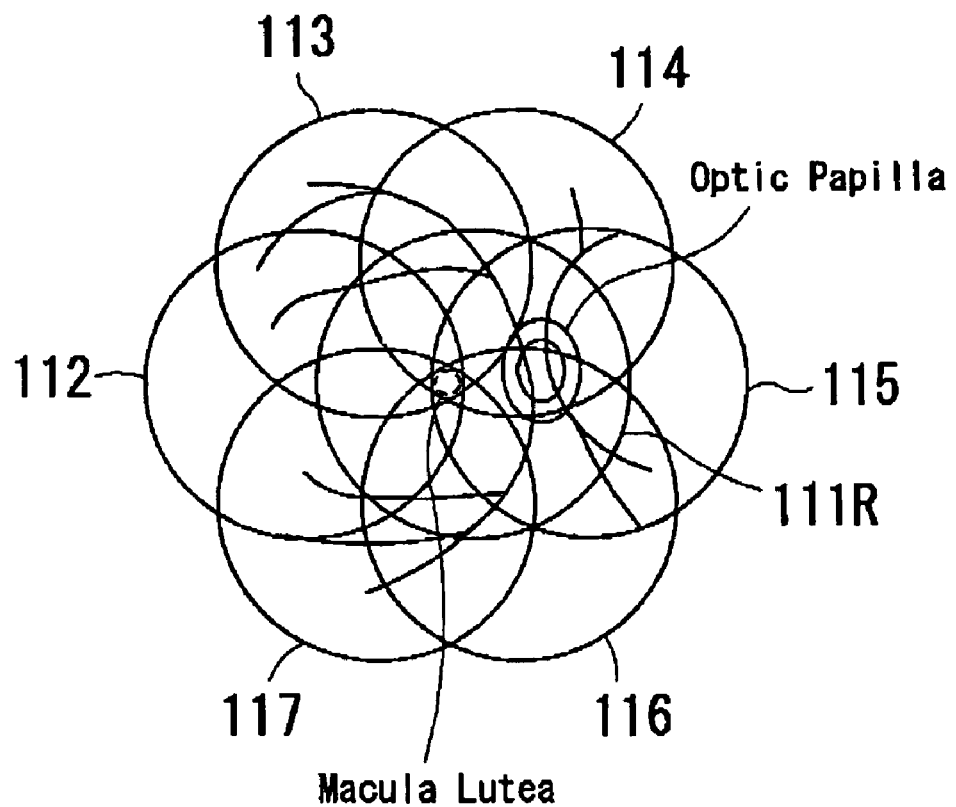

Besides, the position 81L corresponding to the opening 71*a* is a fixation target presenting position used at the time of photographing a central portion of a fundus of a left eye which has its center in the vicinity of a posterior pole including a macula lutea and an optic papilla, and is defined as a reference position at the time of photographing the fundus of the left eye. On the other hand, the position 81R corresponding to the opening 71*b* is a fixation target presenting position used at the time of photographing a central portion of a fundus of a right eye which has its center in the vicinity of a posterior pole, and is defined as a reference position at the time of photographing the fundus of the right eye. Further, the positions 82–87 corresponding to the openings 71*c*–71*h* are fixation target presenting positions (peripheral positions) used at the time of photographing peripheral portions of the fundi of the right and left eyes. FIG. 4B is a view describing regions on the fundus to be photographed when the fixation target is respectively presented in the positions 81R and 82–87 at the time of photographing the fundus of the right eye, where the regions 111R and 112–117 are corresponding respectively to the positions 81R and 82–87.

Incidentally, a reflection mirror 78 is arranged on the other side of the relay lens 36 with respect to the dichroic mirror 37. The reflection mirror 78 is arranged in a position approximately conjugate with an image-pickup surface of the CCD camera 38 via the relay lens 36, and also in a position approximately conjugate with the openings 71*a*–71*h* arranged on the optical axis L2 via the relay lens 75. A part of the fixation target light passing through the openings 71*a*–71*h* is reflected by the dichroic mirror 37 and reflected again by the reflection mirror 78 to be transmitted through the dichroic mirror 37, and photo-received on the CCD camera 38 via the relay lens 36 to form an image of the fixation target. Thereby, a composite image is displayed on the monitor 8, where the image of the fixation target is superimposed on the image of the fundus Ef.

<Control System>

Image signals outputted from the CCD cameras 65, 38 and 35 are inputted to an image processing unit 80. The image processing unit 80 detects the image of the alignment target based on the image signal from the CCD camera 65 and the image of the focus target based, on the image signal from the CCD camera 38. Further, the image processing unit 80 is connected to the monitor 8 to control an image to be displayed thereon. The control unit 90 is connected with the image processing unit 80, the Y-moving unit 6, the X- and Z-moving unit 7, the joystick 4, the moving mechanism 39, the inserting and removing mechanism 27, the pulse motor 73, a photographing switch 83, a switch part 84 having various switches, a rotation switch 85 used in manual focusing, the respective light sources, and the like. (In FIG. 2, connection lines are partly not illustrated.)

Figure 7:
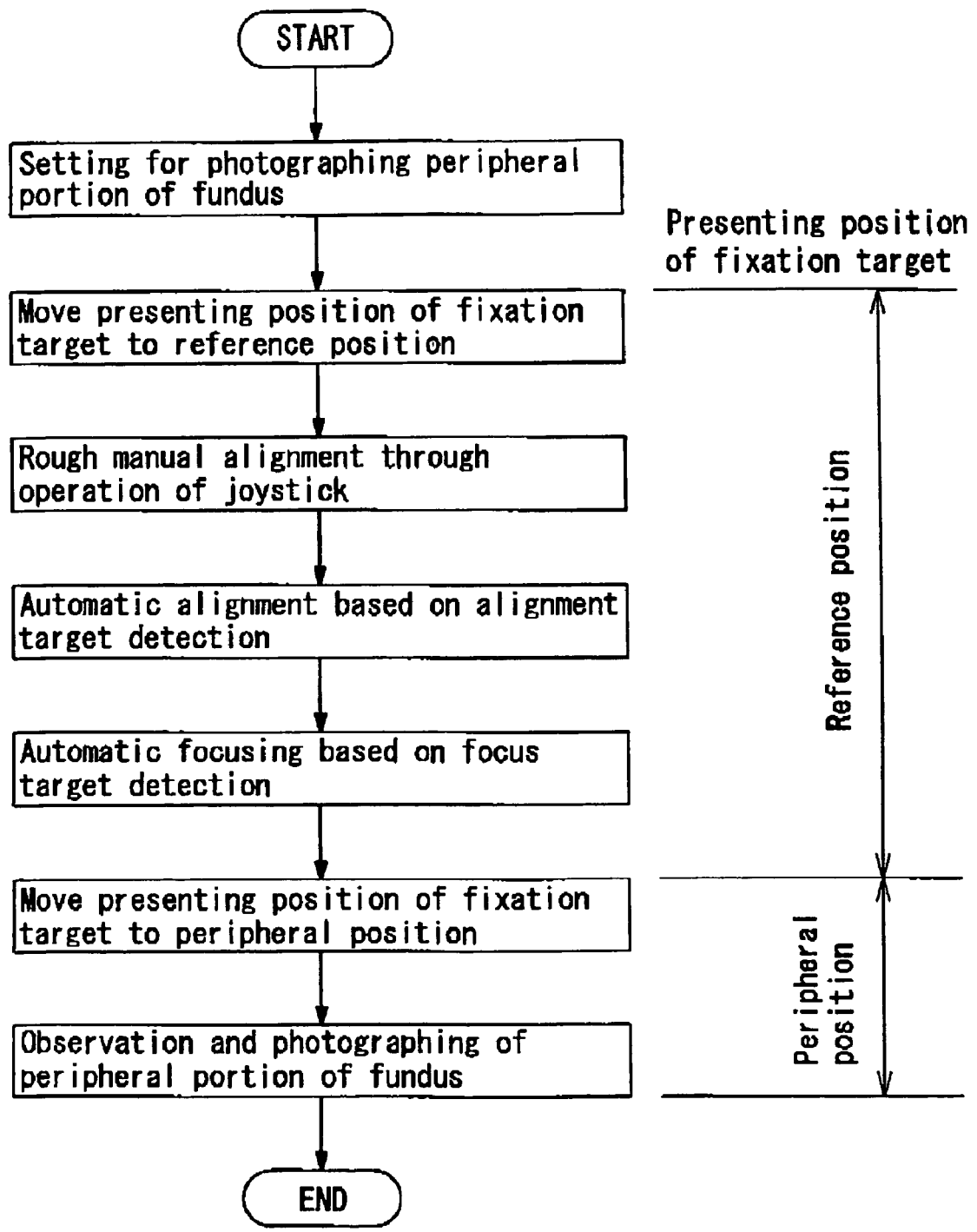
FIG. 7 is a flow chart showing operation of observation and photographing of a peripheral portion of the fundus.
Figure 8A:
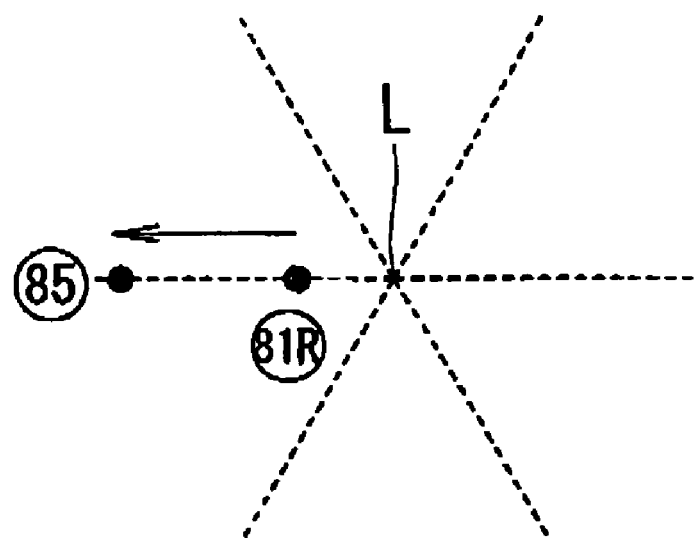
FIGS. 8A and 8B are views showing presenting positions of the fixation target and their corresponding regions on the fundus to be photographed at the time of observation and photographing of the peripheral portion of the fundus.
Figure 8B:
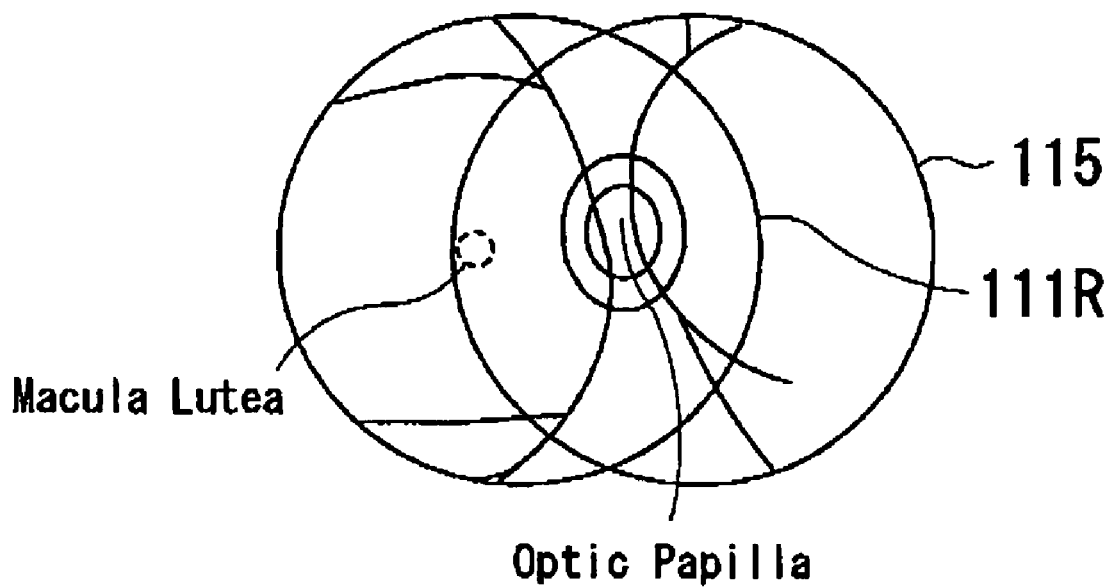

In the apparatus having a constitution as above, the operation thereof will be described hereinafter. Here, a case will be described referring to FIG. 7, where the peripheral portion of the fundus of the right eye is photographed while selecting an automatic alignment mode and an automatic focusing mode with a mode changeover switch 84*a* in the switch part 84. At the time of photographing, the right or left eye is specified with a switch 84*b* for specifying an eye to be photographed. Besides, the specification (changeover) of the eye to be photographed may be detected through detection of movement of the moving base 2 in the X-direction with respect to the base 1 using a micro switch or the like. Also, at the time of photographing, the presenting position of the fixation target is set with a presenting position setting switch 84*c*. Hereinafter, as an example of photographing the peripheral portion of the fundus, a case will be described where the region 115 (see FIG. 8B) is photographed in order to photograph the optic papilla, and the presenting position of the fixation target is set to the position 85.

When a signal for specifying (changing over) the eye to be photographed is inputted to the control unit 90 in the automatic focusing mode, the control unit 90, taking the signal as a trigger, becomes ready to actuate automatic focusing. Becoming ready to actuate the automatic focusing, the control unit 90 controls to arrange the shielding plate 71 having the opening 71*b* in front of the light source 74 to bring the presenting position at the fixation target to the reference position for photographing the fundus of the right eye, even though the presenting position of the fixation target has been set to the peripheral position for photographing the peripheral portion of the fundus. The fixation target light passing through the opening 71b converges on the fundus Ef of the eye E via the relay lens 75 to the objective lens 25, so that the examinee visually identifies the fixation target. A region to be picked up by the CCD camera 39 in this state is the region 111R (see FIG. 8B) having its center in the vicinity of the posterior pole.

Figure 5:
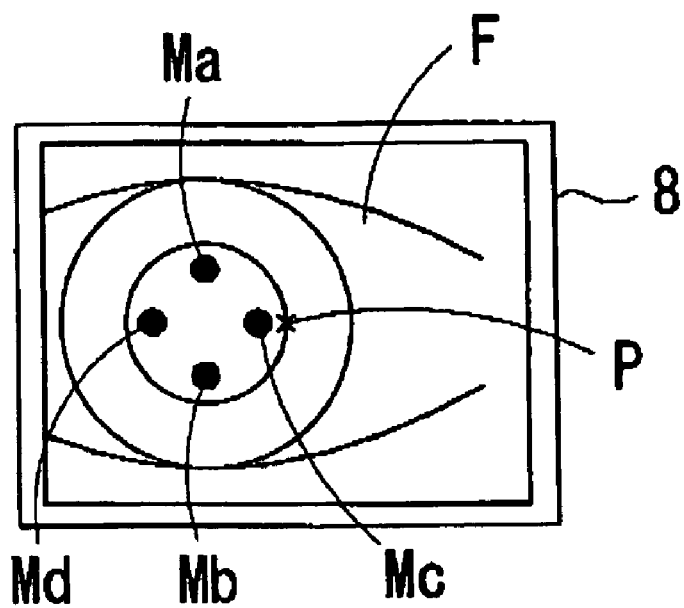
FIG. 5 is a view showing an example of an observation image of an anterior-segment of an eye.

Keeping the eye E made fixate on the fixation target presented in the reference position, the examiner aligns the eye E with the photographing unit 3 while observing the anterior-segment of the eye E. At the time of the observation of the anterior-segment (alignment), the dichroic mirror 24 and the glass plate 23 are inserted into the optical path of the fundus observation/photographing optical system 30 (the optical path between the objective lens 25 and the apertured mirror 22). The image of the anterior-segment of the eye formed by the light source 58 is reflected by the dichroic mirror 24 and picked up by the CCD camera 65. In addition, the image of the alignment target formed by the alignment target projection optical system 50 is also reflected by the dichroic mirror 24 and picked up by the CCD camera 65. The image signal outputted from the CCD camera 65 is inputted to the image processing unit 80, and an image F of the anterior-segment of the eye E and the image of the alignment target are displayed on the monitor 8 (see FIG. 5). In FIG. 5, the target images Ma and Mb vertically positioned are the alignment target images at a finite distance formed by the first projection optical system 51, and the target images Mc and Md horizontally positioned are the alignment target images at an infinite distance formed by the second projection optical system 55. P is a reticle for alignment.

Figure 9:
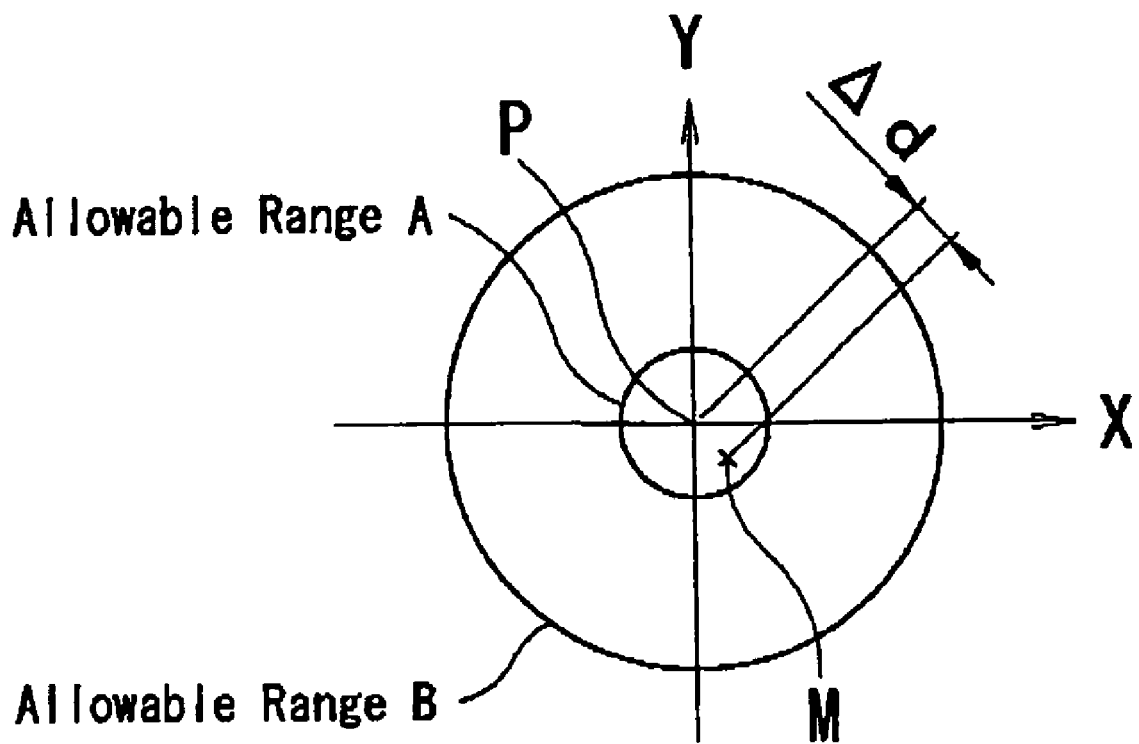
FIG. 9 is a view showing allowable ranges for alignment completion in X- and Y-directions.

The examiner operates the joystick 4 to move the moving base 2 in the X- and Z-directions and the photographing unit 3 in the Y-direction so that the image F of the anterior-segment of the eye E is placed in the center of the monitor 8. Then, when the four target images Ma to Md picked up by the CCD camera 65 are detectable to the image processing unit 80, automatic alignment through driving and control of the X- and Z-moving unit 7 and the Y-moving unit 6 is actuated. The image processing unit 80 detects a corneal center M based on an intersection point of a segment between the target images Ma and Mb and a segment between the target images Mc and Md to obtain a deviation Δd from an alignment reference position P (an alignment state) in the X- and Y-directions as shown in FIG. 9. Upon receiving an output signal from the image processing unit 80, the control unit 90 drives and controls the X- and Z-moving unit 7 and the Y-moving unit 6 to move the photographing unit 3 in the X- and Y-directions so that the deviation Δd in the X- and Y-directions falls within a predetermined allowable range A for alignment completion. Further, the image processing unit 80 compares a distance between the target images Ma and Mb with that between the target images Mc and Md to obtain a deviation from an alignment reference position (an alignment state) in the Z-direction. It utilizes a characteristic that in the case of forming corneal reflection images using a light source at an infinite distance and a light source at a finite distance, if a working distance is changed, a height of the image formed with the light source at a finite distance changes while that formed with the light source at an infinite distance does not change. (For the details, see U.S. Pat. No. 5,463,430 corresponding to Japanese Patent Application Unexamined Publication No. Hei6-46999.) Upon receiving the output signal from the image processing unit 80, the control unit 90 drives and controls the X- and Z-moving unit 7 to move the photographing unit 3 in the Z-direction so that the deviation in the Z-direction falls within a predetermined allowable range for alignment completion (not illustrated).

The infrared illumination light from the illumination optical system for fundus observation is reflected by the apertured mirror 22, is transmitted through the glass plate 23 and the dichroic mirror 24, converges once in the vicinity of the pupil of the eye E by the objective lens 25, and is diffused to be projected onto the fundus Ef. Also, the infrared target light from the focus target projection optical system 40 is reflected by the apertured mirror 22, is transmitted through the glass plate 23 and the dichroic mirror 24 to be projected onto the fundus Ef via the objective lens 25.

The image of the fundus Ef and the image of the focus target are picked up by the CCD camera 38 via the objective lens 25 to the relay lens 36. The image signal outputted from the CCD camera 38 is inputted to the image processing unit 80, and the images of the fundus Ef and the focus target are displayed on the monitor 8.

Figure 6:
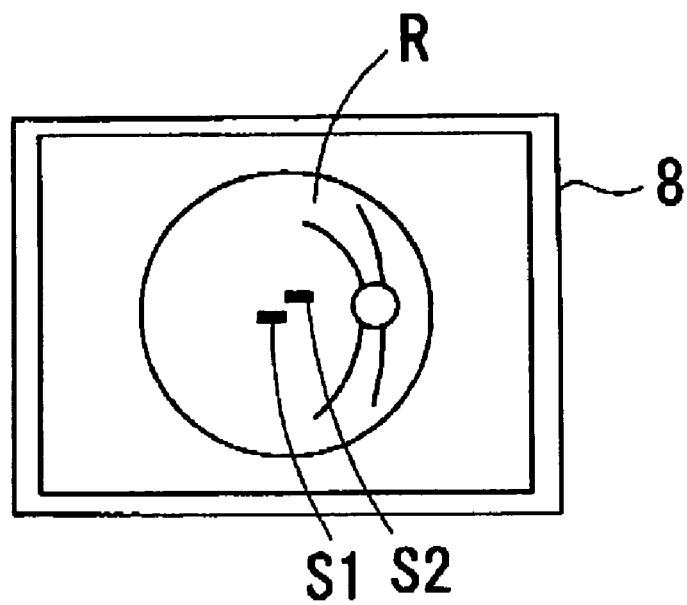
FIG. 6 is a view showing an example of an observation image of the fundus.

FIG. 6 is a view showing an example of the image of the fundus Ef picked up by the CCD camera 38, in which focus target images S1 and S2 are formed at the center of a fundus image R by the focus target projection optical system 40. When the fundus Ef is out of focus, the focus target images S1 and S2 are separated, and when the fundus Ef is brought into focus, the focus target images S1 and S2 coincide with each other. The image processing unit 80 detects the focus target images S1 and S2 and sends their separation information to the control unit 90. Then, the control unit 90 drives and controls the moving mechanism 39 based on the separation information of the focus target images S1 and S2 to move the focusing lens 32 and the target plate 42 in the optical axis direction for bringing focus on the fundus Ef automatically. Since the presenting position of the fixation target is in the reference position when the automatic focusing is actuated, the focus target images S1 and S2 neither chip nor blur, so that the automatic focusing may be performed accurately.

When completion of the automatic alignment in the X-, Y- and Z-directions and completion of the automatic focusing are detected, the control unit 90 controls the monitor 8 to switch a display from the image of the anterior-segment of the eye E picked up by the CCD camera 65 to the image of the fundus Ef picked up by the CCD camera 38. Further, once the automatic focusing is completed, the control unit 90 controls to stop (prohibit) the actuation of the automatic focusing until a signal for instructing the actuation of the automatic focusing is provided (inputted). In a case where the presenting position of the fixation target is set to the position 85, the control unit 90, upon completion of the automatic focusing, drives and controls the pulse motor 73 to automatically arrange the shielding plate 71 having the opening 71f in front of the light source 74 (or, the examiner, upon completion of the automatic focusing, sets the presenting position to the position 85 using the presenting position setting switch 84c). Thereby, the presenting position of the fixation target is brought to the position 85 (see FIG. 8A) to guide a visual axis of the eye E in a direction of the position 85, so that the region 115 is observable and ready to be photographed. Although there may be a case where an eye position inclines and the focus target images S1 and S2 chip or blur, a malfunction of the automatic focusing caused by improper detection of the focus target images S1 and S2 is prevented, since the actuation of the automatic focusing remains to be stopped once the automatic focusing is completed.

Furthermore, after the completion of the automatic alignment in the X-, Y- and Z-directions and the completion of the automatic focusing are detected, the control unit 90 controls to change a condition of the automatic alignment. In other words, as shown in FIG. 9, the actuation of the automatic alignment is stopped (prohibited) until the deviation Δd from the alignment reference position P in the X- and Y-directions extends beyond a second allowable range B which is defined greater than the allowable range A for alignment completion. In the same way, the actuation of the automatic alignment is stopped (prohibited) until the deviation from the alignment reference position in the Z-direction extends beyond a second allowable range which is defined greater than the allowable range for alignment completion. Thereby, it is possible for the examiner to perform fine-adjustment of alignment while observing the image of the fundus Ef.

The examiner observes the image of the fundus Ef displayed on the monitor 8 to perform the fine-adjustment of alignment through operation of the joystick 4 or the like so that an image without a flare may be observed. In addition, fine-adjustment of focusing may be performed by moving the focusing lens 32 through operation of the rotation switch 85. When a desired portion of the fundus Ef becomes favorably observable, the photographing switch 83 is pushed to perform photographing. The control unit 90 drives and controls the inserting and removing mechanism 27 to remove the dichroic mirror 24 and the glass plate 23 from the optical path and make the light source 14 emit light. Thereby, the fundus Ef is illuminated with the visible illumination light, and the visible reflection light from the fundus Ef is photo-received on the CCD camera 35 via the objective lens 25 to the dichroic mirror 34 to form the image of the fundus Ef. The image processing unit 80 switches the monitor 8 to display the image of the fundus Ef picked up by the CCD camera 35. When the image of the fundus Ef is checked and the focusing is unfavorable, photographing may be performed again by the fine-adjustment of focusing through operation of the rotation switch 85.

In a case where the automatic focusing needs to be performed again because, for example, the face of the examinee moves widely, the automatic focusing is made ready to be actuated by pushing an automatic-focusing actuating switch 84*d* to provide the signal for instructing the actuation of the automatic focusing. In addition, the signal for instructing the actuation of the automatic focusing is also provided when a signal from an examinee changeover switch 84*e* for inputting a changeover between examinees, or a signal from the switch 84*b* for specifying an eye to be photographed is inputted.

Among the cases where the peripheral portion of the fundus is observed and photographed, the fundus camera consistent with the present invention is effective especially in such cases that an excavation of the optic papilla and a changing condition on a surface of the optic papilla of a nerve fiber are observed for the purpose of early detection of glaucoma, and that the examinee's eye is reexamined to observe and photograph the same peripheral portion of the fundus that has been once observed and photographed.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera for photographing a fundus of an eye to be examined, the camera comprising:
    a photographing optical system having a photographing optical axis, a focusing lens movable in a direction of the photographing optical axis, and an image-pickup element;
    a lens moving unit which moves the focusing lens in the photographing optical axis direction;
    a focus target projection optical system for projecting a focus target onto the fundus;
    a focus target detection optical system for detecting the projected focus target;
    a fixation target presenting unit which presents a fixation target for guiding a line of sight to the eye, in which a presenting position of the fixation target is changeable between a reference position which is a position for photographing a central portion of the fundus and a peripheral position which is a position for photographing a peripheral portion of the fundus;
    focusing control means for controlling the lens moving unit based on a detection result of the focus target to perform automatic focusing of the photographing optical system with respect to the fundus; and
    fixation target presentation control means for controlling the fixation target presenting unit so that the presenting position of the fixation target is brought to the reference position when the automatic focusing is actuated, even though the presenting position of the fixation target is set to the peripheral position.

2. The fundus camera according to claim 1, further comprising:
    an optical system moving unit which relatively moves the photographing optical system with respect to the eye;
    an alignment detecting unit which detects an alignment state of the photographing optical system with respect to the eye; and
    alignment control means for controlling the optical system moving unit based on a detection result by the alignment detecting unit to perform automatic alignment of the photographing optical system with respect to the eye so that the alignment state may fall within a first allowable range.

3. The fundus camera according to claim 2, wherein the alignment control means, upon completion of the focusing by the focusing control means, stops re-actuating the automatic alignment until the alignment state deviates from a second allowable range which is defined greater than the first allowable range.

4. The fundus camera according to claim 1, wherein the fixation target presentation control means, upon completion of the focusing by the focusing control means, controls the fixation target presenting unit to bring the presenting position of the fixation target to the set peripheral position.

5. The fundus camera according to claim 1, wherein the focusing control means, upon completion of the focusing, stops re-actuating the automatic focusing until a predetermined automatic-focusing instructing signal is inputted thereto.

* * * * *